US006455586B1

(12) United States Patent
Kaplan et al.

(10) Patent No.: US 6,455,586 B1
(45) Date of Patent: *Sep. 24, 2002

(54) TOPICAL IMMUNOMODULATING COMPOSITIONS FOR TREATMENT OF AIDS, HEPATITIS B & C, OTHER INFECTIOUS DISEASES, AND CANCER

(76) Inventors: Leonard L. Kaplan, One Minuteman Ct., East Brunswick, NJ (US) 08316; William R. Levis, 17 Weaver St., Staten Island, NY (US) 10312

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/459,935

(22) Filed: Dec. 13, 1999

Related U.S. Application Data

(60) Provisional application No. 60/112,363, filed on Dec. 15, 1998.

(51) Int. Cl.[7] .................. A61K 31/20; A61K 31/015
(52) U.S. Cl. .................. 514/558; 514/560; 514/763
(58) Field of Search ............................... 514/763, 558, 514/560

(56) References Cited

U.S. PATENT DOCUMENTS 4,020,183 A * 4/1977 Asculai et al. ............ 424/341
4,997,851 A * 3/1991 Isaacs et al. ............... 514/558

FOREIGN PATENT DOCUMENTS

WO 96/32142 * 10/1996 ........... A61L/15/44

OTHER PUBLICATIONS

129CA:130918, Loftsson et al. 1998.*

99CA:181485, Keith, 1982.*

Merck Index, 10th edition, Windholz et al ED., Merck, Dohm & Sharp, Rahway, NJ, abstract #7455. 1984.*

* cited by examiner

*Primary Examiner*—Russell Travers
(74) *Attorney, Agent, or Firm*—Stuart H. Nissim

(57) ABSTRACT

Topical drug compositions, containing contact sensitizing agents as the active components of the subject patent compositions, can provide a pharmacological action that induces a delayed hypersensitization reaction resulting in stimulation of cell mediated immunity when applied to the skin. The preferred composition contains, but is not limited to, Diphenylcyclpropenone as a preferred embodiment of the class of contact sensitizing drugs applied to the skin in an optimally prepared pharmaceutical formulation with controlled absorption properties to reach the peripheral circulation resulting in increases in CD4+ helper T cells of benefit to immunocompromised patients.

6 Claims, No Drawings

TOPICAL IMMUNOMODULATING COMPOSITIONS FOR TREATMENT OF AIDS, HEPATITIS B & C, OTHER INFECTIOUS DISEASES, AND CANCER

This final patent application filing is a continuation of the Provisional Patent Application No. 60/112,363 dated Dec. 15, 1998.

BACKGROUND OF THE INVENTION

Contact sensitizers such as dinitrochlorobenzene (DNCB) have been reported to raise CD4+ helper T cell counts and reduce viral load in HIV positive patients (1,2). The DNCB was applied to the skin in 10% concentration dissolved in the volatile solvent acetone which resulted in unreliable and unpredictable contact sensitization reactions. Biologically, increases in CD+ helper T cell counts are accompanied by variable decreases in HIV retroviral replication as measured by human immunovirus ribonucleic acid (RNA) levels in dendritic cells that are the primary antigen presenting cells of the human immune system. It is the dendritic cells and microphages that are infected during the initial phases of human immunovirus growth in AIDS patients. Optimally formulated contact sensitizers when topically applied, can induce TH-1 type immunity by releasing cytokines including Interleukin 2, valuable in treating hepatitis B&C, and forms of cancer as well as AIDS. On the other hand, the medical use of the preferred contact sensitizer diphenylcyclopropenone has been limited primarily to the treatment of alopecia areata as disclosed in referenced U.S. Pat. No. 4,985,464 wherein the volatile solvent acetone with unreliable absorption properties was used as the formulation vehicle. Other contact sensitizers referenced in the literature (3) are, but not limited to, squaric acid dibutylester, urishiol, oxazolone, dinitrofluorobenzene, and paraphenylenediamine. In all referenced cases, the volatile solvent acetone with unreliable absorption characteristics was used as the drug delivery system for the contact sensitizers. Accordingly, there is a need for a more reliable stabilized composition in which the contact sensitizers are soluble and will be reliably and predictably absorbed through the skin to reach the aforementioned dendritic cells of the dermis.

SUMMARY OF THE INVENTION

This invention provides compositions for the topical application of contact sensitizers in a unique topical pharmaceutical emulsion drug delivery system to reliably penetrate the epidermis of immunocompromised human patients in order to stimulate the release of CD4+ helper T cells and induce TH-1 type immunity by releasing cytokines including Interleukin 2, valuable in treating AIDS, Hepatitis B&C, other viral infectious diseases, and Cancer. The compositions contain controlled amounts of diphenylcyclopropenone, dinitrochlorobenzene, dinitrofluorobenzene, squaric acid dibutylester, urishiol, oxazolone, paraphenylene-diamine or other medically useful contact sensitizers emulfified in a non-toxic drug delivery system formula consisting of pharmaceutically acceptable non-volatile, non-ionic surfactants and pharmaceutically acceptable emollients at optimized levels wherein the contact sensitizer(s) are reliably absorbed through the epidermis to reach the dendritic cells in the dermis during the early stages of viral infections in immunocompromised patients. A preferred embodiment of the invention includes diphenylcyclopropenone as the contact sensitizer uniquely formulated in a microemulsified drug delivery sytem consisting of the non-ionic surfactant polyoxyethylene 20 sorbitan momooleate and the emollients isopropyl myristate and/or isopropyl palmitate.

DETAILED DESCRIPTION OF THE INVENTION

The immunmodulating compositions of this invention treat viral infections embodied by AIDS, Hepatitis B&C, other viral infectious diseases and certain types of cancer wherein the the patient's immune system is attacked by the disease. The active ingredients in these compositions are those that are classified pharmacologically as contact sensitizers such as dinitrochlorobenzene, dinitrofluorobenzene, diphenylcyclopropenone, oxazolone, paraphenylenediamine, squaric acid dibutylester, urushiol and the like that are generally recognized as pharmacologically active contact sensitizers. Topically applied, contact sensitizers have been shown to raise the CD4+ helper T cell counts and variably reduce viral load in HIV positive patients when applied as a concentrated solutions in Acetone as the vehicle (1,2,3).

Acetone is a volatile and highly inflammable organic liquid with an LD/50 of 10.7 mg/Kg in rodents and may be classified as a toxic material with repeated human use causing epidermal erythema, dryness, headache, bronchial irritation, CNS effects including fatigue and excitement and with chronic use narcosis. In addition, due to its high vapor pressure and volatility, the contact sensitizer/Acetone solutions when applied to the skin can result in variable, inconsistent and unreliable levels of contact sensitizer absorption through the skin.

In order for the topically applied contact sensitizers to be optimally safe and effective in raising the CD4+ helper T cell counts and reduce viral loads, we found unexpectedly that the topical compositions of this invention consisting of medically accepted contact sensitizers microemulsified in drug delivery vehicles of non-volatile, non-toxic combinations of non-ionic surfactants and cosmetically acceptable emollient esters of fatty esters embodied by isopropyl myristate and isopropyl palmitate result in consistent and reliable absorption of the contact sensitizers through the epidermis to the dendritic cells of the dermis as demonstrated by increases in CD4+ helper T cell counts and reductions in serum viral loads in AIDS patients.

The drug compositions of this invention accordingly may contain non-ionic surfactants of the following classes:

Polyoxyethylene (POE) sorbitan fatty acid esters identified generically as POE 20 sorbitan monolaurate, POE 4 sorbitan monolaurate, POE 20 sorbitan monopalmitate, POE 20 sorbitan monostearate, POE 20 sorbitan monooleate, POE 5 sorbitan monooleate, POE 20 sorbitan trioleate and the like that are oily liquids with low vapor pressure properties and therefore non-volatile and non-irritating to the skin and have the property of emulsifying immiscible combinations of the active ingredient contact sensitizers and the emollient co-solvents embodied by the following alcoholic esters of myristic and palmitic fatty acids:

Isopropyl myristate consisting of esters of isopropyl alcohol and saturated high molecular weight fatty acids, principally myristic acid; and Isopropyl palmitate consisting of esters of isopropyl alcohol and saturated high molecular weight fatty acids, principally palmitic acid, and other like alcohol esters of saturated high molecular weight fatty acids that are mobile oily liquids at room temperature and are miscibly emulsified with the polyoxyethylene sorbitan fatty acid esters embodied in this invention to provide non-toxic, non-volatile topical drug delivery vehicles for the contact sensitizers of this invention.

The drug compositions of this invention are best administered to the skin under an occlusive or semi-occlusive patch to permit localized absorption of the contact sensitizer contained in optimized pharmaceutical vehicles as described in the following examples:

| | |
|---|---|
| (1) Dinitrochlorobenzene | 0.001% |
| Polyoxyethylene 20 sorbitan monolaureate | 50.000 |
| Isopropyl palmitate | 49.999 |

Apply 0.1 ml to 1.0 ml to an absorbent pad bonded to a polyvinyl chloride backing with adhesive to be applied to the skin surface

| | |
|---|---|
| (2) Diphenylcyclopropenone | 0.001% |
| Polyoxyethylene 20 sorbitan monooleate | 50.000 |
| Isopropyl myristate | 49.999 |

Apply 0.1 ml to 1.0 ml to a cellulosic pad bonded to a cotton backing with adhesive to be applied to the skin surface

| | |
|---|---|
| (3) Squaric Acid Dibutylester | 0.005% |
| Polyoxyethylene 20 sorb.monopalmitate | 85.995% |
| Isopropyl myristate | 14.000% |

Apply 0.25 ml to 1.00 ml to a non-woven textile pad bonded to an occlusive backing with adhesive to be applied to the skin surface

| | |
|---|---|
| (4) Diphenyylcyclopropenone | 0.400% |
| Polyoxyethylene 20 sorbitan monoleate | 99.600% |

Apply 0.05 ml to 0.5 ml to an absorbent pad bonded to a to a suitable occlusive or semi-occlusive backing with adhesive to be applied to the skin surface

| | |
|---|---|
| (5) Squaric Acid Dibutylester | 0.010% |
| Polyoxyethylene 4 sorbitan monolaurate | 99.990% |

Apply 0.1 ml to 1.0 ml to cotton pad bonded to a suitable backing with adhesive for controlled absorption when applied to the skin.

These composition examples are cited to demonstrate, but not to limit, various concentrations of active contact sensitizers in non-volatile vehicles applied to the skin by means of various absorbent pads under occlusive or semi-occlusive backings serving as patch applications for administration of the sensitizers to the skin surface.

Other examples of contact sensitizers applicable to formulation in the unique non-volatile, non-irritating, skin absorble vehicle compositions are as follows:

Oxazolone
Fluoroscine isothiocyanate
Dinitrofluorobenzene
Beryllium
Nickel Chloride
Trinitrochlorobenzene
Urishiol

Paraphenylenediamine and the like.

As examples of the HIV viral load reducing effects of the subject compositions, two patients were sensitized with 0.400% diphenylcyclopropenone in a vehicle consisting of equal parts of polyoxyethylene sorbitan 20 monooleate and isopropyl myristate and subsequently rechallenged with 0.100% diphenylcyclopropenone in the same vehicle two weeks, four weeks and eight weeks later. HIV-1 RNA copies per 1.0 ml plasma are shown in Table (1):

TABLE (1)

| HIV-1 RNA Copies/1.0 ml Plasma | |
|---|---|
| Patient #1 | |
| Baseline | 400 Copies |
| Two Weeks | 118 |
| Four Weeks | 60 |
| Eight Weeks | 79 |
| Patient #2 | |
| Baseline | 440 |
| Eight Weeks | 351 |

What is claimed is:

1. A method of treating HIV in a patient in need thereof comprised of topically applying an anhydrous, non-toxic absorbable composition to provide therapeutically effective systemic treatment, said composition consisting of a contact sensitizer selected from the group consisting of dinitrochlorobenzene, dinitrofluorobenzene, diphenylcyclopropenone, oxazolone, paraphenylenediamine, squaric acid dibutylester, and urushiol, and a carrier comprised of a first co-solvent selected from the group consisting of polyoxyethylene 20 sorbitan monolaurate, polyoxyethylene 4 sorbitan monolaurate, polyoxyethylene 20 sorbitan monopalmitate, polyoxyethylene 20 sorbitan monostearate, polyoxyethylene 20 sorbitan monooleate, polyoxyethylene 5 sorbitan monooleate, polyoxyethylene 20 sorbitan triologate, and combinations thereof, and a second co-solvent selected from the group consisting of isopropylmyristate, isopropyl palmitate and combinations thereof.

2. The method of claim 1 wherein said contact sensitizer is diphenylcyclopropenone.

3. The method of claim 1 wherein said contact sensitizer compromises from about 0.002% to about 1.000% weight to volume of said composition.

4. The method of claim 1 wherein said first co-solvent is polyoxyethylene 20 sorbitan monolaurate or polyoxyethylene 20 sorbitan monooleate.

5. The method of claim 1 wherein said second co-solvent is isopropyl myristate or isopropyl palmitate.

6. The method of claim 1 wherein said composition is first applied to the skin of said patient and secondly covered by an absorbent pad under an occlusive or semi-occlusive backing for localized administration of said contact sensitizer for absorption through the skin.

* * * * *